US00PP13265P2

(12) United States Plant Patent
Olesen et al.

(10) Patent No.: US PP13,265 P2
(45) Date of Patent: Nov. 26, 2002

(54) MINIATURE ROSE PLANT NAMED 'POULCEL'

(76) Inventors: L. Pernille Olesen, Hillerodvejen 49, Fredensborg (DK), DK-3480; Mogens N. Olesen, Hillerodvejen 49, Fredensborg (DK), DK-3480

( * ) Notice: Subject to any disclaimer, the term of this patent is extended or adjusted under 35 U.S.C. 154(b) by 80 days.

(21) Appl. No.: 09/608,558

(22) Filed: Jun. 30, 2000

(51) Int. Cl.[7] ..... A01H 5/00

(52) U.S. Cl. ..... Plt./118

(58) Field of Search ..... Plt./118

(56) References Cited

PUBLICATIONS

Canadian Food Inspection Agency "Applications Accepted for Filing" Plant Varieties Journal, 1999. 1 page. Canada.
UPOV–ROM GTITM Computer Database, 2001/02 GTI Jouve Retrieval Software, citation for 'POULcel'.*

* cited by examiner

*Primary Examiner*—Bruce R. Campell
*Assistant Examiner*—Susan B. McCormick

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULhi003'.

The new rose may be distinguished from its seed parent, an unnamed seedling, by the following combination of characteristics:

1. The unnamed seed parent is a large-flowered floribunda with yellow flowers, while 'POULhi003' is a yellow miniature.

2. The unnamed seed parent resulted from a crossing of Fragrant Delight, an orange-salmon floribunda rose, and 'POULsun', a rose variety with U.S. Plant Pat. No. 9,716.

The new variety may be distinguished from its pollen parent, an unnamed seedling, created by the same inventors, by the following combination of characteristics:

1. The unnamed seed parent is a floribunda with dark-yellow colored flowers and more vigorous growth than 'POULhi003'.
2. The unnamed seed parent resulted from a crossing of Arthur Bell, a yellow floribunda rose, and 'POULdom', a yellow floribunda from the same inventors.

The objective of the hybridization of this rose variety for commercial greenhouse culture was to create a new and disinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi003' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi003' was selected by the inventors as a single plant from the progeny of the hybridization in Spring, 1996.

Asexual reproduction of 'POULhi003' by cuttings and traditional budding was first done by L. Pernille and Mogens N. Olesen in Fredensborg, Denmark, in July 1996. This initial and other subsequent propagations conducted in controlled environments have demonstrated that the characteristics of 'POULhi003' are true to type and are transmitted from one generation to the next.

BRIEF DESCRIPTION OF THE DRAWING

In response to a mandate from the European Union Community Plant Variety Office, the denomination of the instant cultivar has been changed, from 'POULcel' to 'POULhi003'. The accompanying color illustration shows as true as is reasonably possible to obtain in color photographs of this type, the typical characteristics of the buds, flowers, leaves, stems, and a plant of 'POULhi003'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULhi003', as observed in its growth in glasshouses in Half Moon Bay, Calif., on plants aged 16 weeks. Color references are made using The Royal Horticutural Society (London, England) Colour Chart, 1995, except where common terms of color are used. For a comparison, several physical characteristics of the rose variety 'POULsun', a yellow miniature rose variety from the same inventors described and illustrated in U.S. Plant Pat. No. 9,716 and issued on Dec. 3, 1996 are compared to 'POULhi003' in Chart 1.

CHART 1

| | 'POULhi003' | 'POULsun' |
|---|---|---|
| Flower bud color. | Yellow Group 11C. | Yellow Group 13A. |
| Flower Petal Count. | Semi-Double. Average of 17 to 19 petals. | Double. Average of 30–35 petals. |
| Prickles on stems. | Few to none. Approx. 1 mm in length. Linear. | Ordinary quantity. Approx. 6 mm in length. With downward hook. |

Parents: Unnamed seedling×Unnamed seedling.
Classification:
*Botanical.*—*Rosa hybrida.*
*Commercial.*—Miniature rose.

FLOWER AND FLOWER BUD

Blooming habit: Recurrent.
Flower bud:
*Size.*—Upon opening, 20 mm to 23 mm in length from base of receptacle to end of bud.
*Bud form.*—Pointed ovoid. Shape from side at ¼ open is rectangular.
*Bud color.*—As sepals unfold, bud is Yellow Group 11c with intonations of Orange Group 29B–C on upper ⅓ of bud. Basal area of bud with intonations of Yellow-Green Group 144C. At ¼ opening, outermost petals are Yellow Group 11C with intonations of Orange Group 29 B–C.
*Sepals.*—Sepal length is 12 to 15 mm. Sepal width is 6 to 8 mm. Coloration is Green Group 137A. Strong foliaceous appendages on three of the five sepals. Surfaces of sepals slightly pubescent. Stipitate glands are present on margins of sepals.
*Receptable.*—Surface: Smooth. Shape: Funnel shaped. Size: Medium. 6 to 7 mm (h)×6 to 7 mm (w). Color: Green Group 144B.
*Peduncle.*—Surface: Smooth, with limited numbers of stipitate glands. Length: 45 to 70 mm average length. Color: Green Group 144A. Strength: Upright.
Borne.—Generally singly, with 1–2 buds per flowering stem.
Flower bloom:
*Fragrance.*—Light floral fragrance.
*Duration.*—As a pot plant, flowers last from 8 to 11 days. As a cut flower 5 to 7 days.
*Size.*—Medium flowers for a 12 cm pot rose. Average flower diameter is 45–50 mm when open.
*Form.*—Shape of flower when viewed from the side: Upon opening, upper part: Flat. Upon opening, lower part: Convex. Open flower, upper part: Flattened convex. Open flower, lower part: Flattened convex.
*Petalage.*—Semi-double. Average range: 17–19 petals under normal conditions with 3–4 petaloids.
Color:
*Upon opening, petals.*—Petals: Upper Surface: Yellow Group 2D at middle and marginal zones.Green Yellow 1B at basal zone. Reverse Side: Yellow Group 2D at middle and marginal zones. Intonations of Red Group 37C and Green-Yellow Group 1B at the basal zone. Outermost petals with stronger intonations of Green Group 144C.
*Upon opening, basal petal spots.*—No distinctive coloration at petal base observed.
*After opening, petals.*—Petals: Upper Surface: Yellow Group 10A–C with light intonations of Red Group 37A at marginal zone. Green intonations at base lacking. Reverse Side: Yellow Group 6A–C with strong intonations of Red Group 137A throughout.
*Upon opening, basal petal spots.*—No distinctive coloration at petal base observed.
General tonality: On open flower the blend of colors on the upper and reverse sides of the petal give the bloom the general tonality of Yellow-Orange 18A. No change in the general tonality at the end of the third day.
Petals:
*Petal reflex.*—Slight reflex.
*Petal margin.*—Uniform.
*Shape.*—Round.
*Petaloids.*—Present. Generally 3–4.
*Thickness.*—Average.
*Arrangement.*—Informal.
Reproductive organs:
*Pollen.*—Color: Yellow-Orange Group 23B. Abundance: Very abundant.
*Anthers.*—Size: 2 mm long. Color: Yellow Group 7A.
*Filaments.*—Color: Yellow Group 7A. Length: 3 to 5 mm. Quantity: 35 to 40.
*Stigmas.*—Stigmas are at same position as anthers. Color: Green-Yellow Group 1C. Quantity: 35 to 40.
*Styles.*—Color: Green-Yellow Group 1C. Length: 3 to 5 mm.

PLANT

Plant growth: Compact, upright to bushy. When grown as a 12 cm pot plant, the average height of the plant itself is 23 cm and the average width is 22 cm. When grown as a budded field grown plant on multiflora understock, the average height of the plant itself is 35 cm and the average width is 33 cm.
Stems:
*Color.*—Young wood: 144A. Older wood: 144A.
*Prickles.*—Incidence: Very few. Size: Average length: 1 mm. Color: Translucent. Shape: Linear.
*Surface.*—Young wood; Smooth. Older wood: Smooth.
*Length.*—Stem length is 30 cm on average. Internode length is 3 to 5 cm.
Plant foliage:
*Normal number of leaflets on normal leaves in middle of the stem.*—5 leaflets.
*Leaf size.*—Medium; 95 mm (l)×65 mm (w).
*Abundance.*—Average.
*Color.*—Upper Leaf Surface: Green Group 139A. Lower Leaf Surface: Green Group 137D. Juvenile foliage: Green Group 139A. Anthocyanin intonation: Location: Margins of leaflets, sepals, and young shoots. Color: Greyed-Red Group 181B.

Plant leaves and leaflets:

*Stipules.*—Size: 15 mm in length. Color: Yellow-Green Group 144C on inside; Yellow-Green Group 144A on marginal zones.

*Petiole.*—Length: 23 mm in length. Color: Yellow-Green Group 144A. Underneath: Yellow-Green Group 144B. Margins: Green Group 149A.

*Rachis.*—Color: Yellow-Green Group 144A. Underneath: Yellow-Green Group 144B. Margins: Green Group 149A.

*Leaflet.*—Edge: Serrated. Shape: Ovoid. Texture: Moderately glossy, thin and leathery. Other: On plants grown under hight light conditions, margins with intonations of Greyed-Red Group 181B.

Disease resistance: Average resistance to mildew, black spot, and Botrytis under normal growing conditions in Half Moon Bay, Calif.

Cold hardiness: 'POULhi003' has been found to be resistant to damage from cold, heat and drought in USDA Zone 7.

We claim:

1. A new and distinct variety of rose plant of the miniature class, substantially as herein illustrated and described as a distinct and novel rose variety due to its abundant yellow flowers, compact growth, year round flowering under glasshouse conditions, suitability for production from softwood cuttings in pots, and durable flowers and foliage which make the variety suitable for distribution in the floral industry.

* * * * *

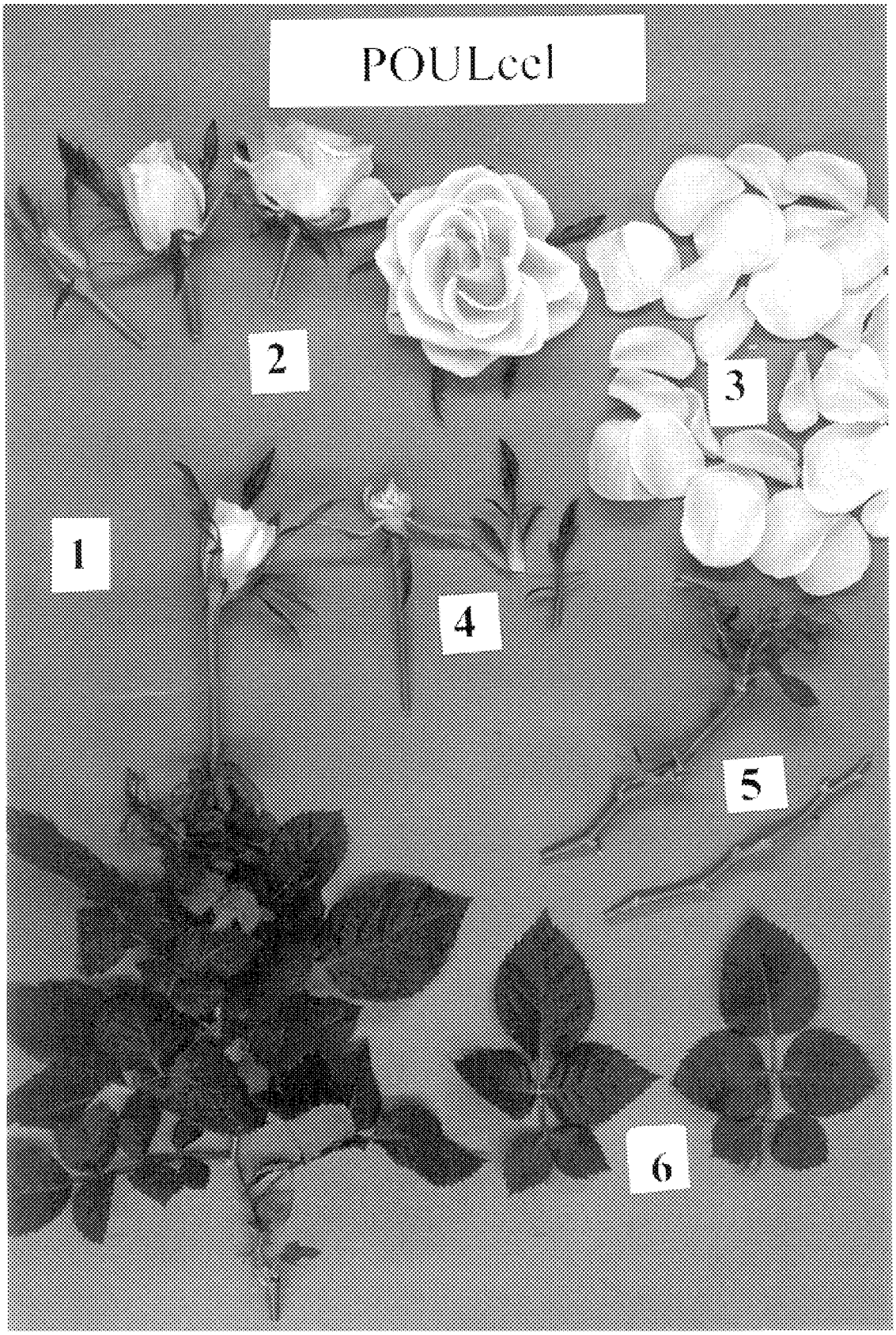
POULcel
1
2
3
4
5
6